United States Patent [19]

Kondo et al.

[11] 4,237,058

[45] Dec. 2, 1980

[54] BICYCLIC LACTONE DERIVATIVES

[75] Inventors: Kiyoshi Kondo; Toshiyuki Takashima; Minoru Suda, all of Kanagawa, Japan

[73] Assignee: FMC Corporation, Philadelphia, Pa.

[21] Appl. No.: 90,218

[22] Filed: Nov. 1, 1979

[51] Int. Cl.$^3$ ............................................. C07D 307/93
[52] U.S. Cl. ........................... 260/343.3 R; 260/343.5; 562/506
[58] Field of Search ................................. 260/343.3 R

[56] References Cited

U.S. PATENT DOCUMENTS

| | | | |
|---|---|---|---|
| 3,723,469 | 3/1973 | Martel | 560/124 |
| 4,014,918 | 3/1977 | Martel | 260/343.21 |
| 4,024,163 | 5/1977 | Elliott et al. | 260/347.4 |
| 4,132,717 | 1/1979 | Roman | 260/343.3 R |
| 4,166,063 | 8/1979 | Martel et al. | 260/343.3 R |

FOREIGN PATENT DOCUMENTS 868445 12/1978 Belgium .
3666 8/1979 opean Pat. Off. .

OTHER PUBLICATIONS

Osborn et al. Jour. American Chem. Soc. 90, p. 5806, 1968.
March, Advanced Organic Chem., McGraw-Hill, p. 632.
Krap Cho, Jour. Org. Chem., vol. 43, 1978, p. 138.
Nozaki et al. Tetrahedron vol. 24, p. 3661, 1968.

Primary Examiner—Henry R. Jiles
Assistant Examiner—Jane T. Fan
Attorney, Agent, or Firm—Robert L. Andersen; Robert M. Kennedy; H. Robinson Ertelt

[57] ABSTRACT

Novel intermediates for production of insecticidal cis-3-(2,2-disubstituted-ethenyl)-2,2-dimethylcyclopropanecarboxylates, processes for preparing the intermediates, and processes for preparing the final product insecticides via a novel bicyclic lactone intermediate are described and exemplified.

1 Claim, No Drawings

BICYCLIC LACTONE DERIVATIVES

This invention relates to novel intermediates for production of insecticidal cis-3-(2,2-disubstituted-ethenyl)-2,2-dimethylcyclopropanecarboxylates and to processes for preparing the intermediates.

U.S. Pat. No. 4,024,163 discloses 3-(2,2-dihaloethenyl)-2,2-dimethylcyclopropanecarboxylic acids, lower alkyl esters thereof, and insecticidal pyrethroid esters made from them. The intermediate acids may be converted to insecticidaly active pyrethroids by treatment with thionyl chloride to produce a corresponding acid chloride, followed by reaction with an appropriate alcohol, such as 3-phenoxybenzyl alcohol, to produce the corresponding insecticidal ester.

These esters and acids are known to exist as cis and trans geometrical isomers; and it is also known that the cis isomers of a given dihaloethenylcyclopropanecarboxylate are generally more active insecticidally than the correponding trans isomers. As a result, substantial research effort has been directed to processes for producing cis geometrical isomers of these acids and esters, substantially free of trans acids or esters.

Belgian Pat. No. 868,445, published Dec. 12, 1978 discloses the use of a bicyclic lactone of the formula

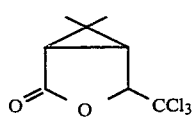
(A)

as an intermediate in the preparation of cis-3(2,2-dihaloethenyl)-2,2-dimethylcyclopropanecarboxylic acid, an intermediate for the corresponding cis-pyrethroid. The bicyclic lactone is prepared by reacting caronaldehydic acid with a haloform, then dehydrating the resulting acid. The caronaldehydic acid used as a starting material, and processes for its preparation are disclosed in U.S. Pat. Nos. 3,723,469 and 4,132,717.

In one aspect of the present invention there is provided a novel compound of formula I

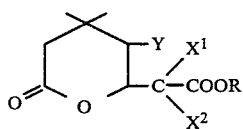
(I)

and a process for its preparation. In another aspect of the present invention there is provided a novel bicyclic lactone of formula II

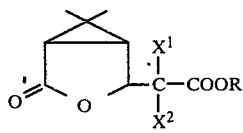
(II)

and a method for its preparation. In another aspect of the present invention there is provided a method for producing a cis-cyclopropanecarboxylic acid such as cis-3-(2,2-dihaloethenyl)-2,2-dimethylcyclopropanecarboxylic acid or cis-3-(2-halo-2-trihalomethylethenyl)-2,2-dimethylcyclopropanecarboxylic acid by simultaneous ring opening and decarboxylation of the bicyclic lactone (II).

Throughout the specification and claims, unless a contrary meaning is specified, the terms halo or halogen mean bromine, chlorine or fluorine which may be independently selected. Similarly the term "lower" as applied to a hydrocarbyl group means having 1 to 4 carbon atoms, straight or branched chain.

The first aspect of this invention comprises a compound of the formula

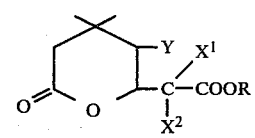
(I)

wherein Y is a chlorine or bromine atom; $X_1$ and $X_2$ are the same or different and each is a halogen atom, a trichloromethyl group, or a trifluoromethyl, and R is an alkyl group of 1 to 4 carbon atoms, preferably methyl or ethyl, with the proviso that Y is a bromine atom when at least one of $X^1$ and $X^2$ is a bromine atom. Preferred compounds are those in which $X^1$ is chlorine or bromine and $X^2$ is the same as $X^1$ or is trifluoromethyl. The compounds of formula I are prepared by reacting 3,4-dihydro-4,4-dimethyl-2H-pyran-2-one with a lower alkyl haloacetate as follows; R, $X^1$, $X^2$, and Y being as specified above:

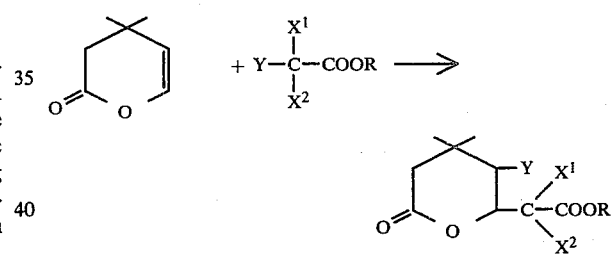

The addition of the haloacetate radical to the C-6 position, rather than the C-5 position of the dihydropyranone is quite surprising. It is known that free radicals having an unpaired electron α to an -OR grop (C-6 of the dihydropyranone may be considered α to an OR group) have increased stability at that α-position. See J. March, *Advanced Organic Chemistry*, 2nd ed., p. 632, McGraw-Hill, N.Y. (1967, 1968). One would thus expect radical addition to occur at the unstabilized C-5 position. Once the actual course of reaction is known, steric hindrance due to the gem-dimethyl group could be postulated as hindering addition at C-5, leading to addition at C-6, but no reference has been found which would enable one skilled in the art to predict with the required degree of certainty whether, or to what extent, the gem-dimethyl group would be expected to influence the addition. Thus, the results achieved are unexpected since one would not have predicted in advance the course the reaction took.

The foregoing reaction is conducted in the presence of a suitable addition catalyst. Suitable catalysts include free radical initiators, light, a transition metal salt, or a complex between a transition metal salt and electron donors such as organic amines, carbon monoxide, acetylacetone, and the like.

Suitable free radical initiators include azobisisobutyronitrile (AIBN), benzoyl peroxide (BPO), acetyl peroxide, di-t-butyl peroxide, t-butyl peracetate, t-butyl perbenzoate, t-butyl perphthalate, t-butyl hydroperoxide and the like.

Suitable transition metal salts which may be employed include cuprous chloride, cupric chloride, ferrous chloride, ferric chloride, cobalt, nickel, zinc, palladium, rhodium or ruthenium chloride, copper cyanide, copper thiocyanide, copper oxide, copper sulfide, copper or iron acetate, iron citrate, iron sulfate, iron oxide, copper or iron acetylacetonate and the like. Cuprous chloride is preferred.

Examples of organic amines which can be used in conjunction with these transition metal salts include aliphatic amines such as n-butylamine, diisopropylamine, triethylamine, cyclohexylamine, ethylenediamine and the like; aromatic amines such as aniline or toluidine; or amine salts such as diethylamine hydrochloride.

The reaction is preferably conducted at elevated temperature, suitably above about 100° C., advantageously in the range of 100°-300° C., more preferably about 150° C. to about 175° C.

The haloacetate and dihydropyranone are suitably used in about equimolar amounts, but an excess of either may be used if desired.

The haloacetate is prepared by esterification of commercially available trihaloacetates or by procedures or from compounds described in J. Am. Chem. Soc., 78, 5639 (1956); Bull. Acad. Sci. USSR 1966, 2049 (1966); or C. A. 73, 87470g (1970) and German Offenlegungschrift No. 1,900,758 referred to therein.

Another aspect of this invention comprises a novel bicyclic lactone of the formula

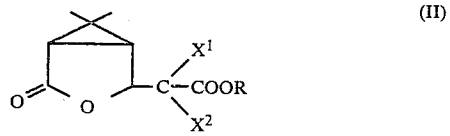

in which $X^1$ and $X^2$ are the same or different and each is a halogen atom, a trichloromethyl group, or a trifluoromethyl group; and R is an alkyl group of 1 to 4 carbon atoms, preferably methyl or ethyl. In the preferred embodiment $X^1$ is bromine or chlorine and $X^2$ is the same as $X^1$ or is trifluoromethyl.

This compound is prepared by reacting the compound of formula I with a base to remove one molar equivalent of hydrogen halide per mole of I.

The base employed in this reaction is suitably an alkali metal alkoxide or hydride. For example, one may employ such alkoxides as sodium methoxide, sodium ethoxide, sodium t-butoxide, potassium t-butoxide, sodium t-pentoxide, or potassium t-pentoxide. The preferred bases are the tertiary alkoxides of 4 or 5 carbon atoms such as sodium t-butoxide. About one molar equivalent per mole of substrate (I) or a slight molar excess of base may be employed. Other strong bases such as sodium hydride may also be suitable.

The reaction is suitably conducted in the presence of a solvent. A wide range of solvents may be employed, including alkanols having 1 to 6 carbon atoms, such as methanol, ethanol, t-butanol, or t-pentanol; ethers having 4 to 6 carbon atoms, such as diethyl ether, tetrahydrofuran, dimethoxyethane or dioxane; or aromatic hydrocarbons of 6 to 10 carbon atoms, such as benzene or toluene.

This dehydrohalogenation reaction is suitably conducted at about room temperature or below, for example at a temperature in the range of −25° C. to about 30° C.

In accordance with another aspect of the invention a cis isomer of a compound of formula III

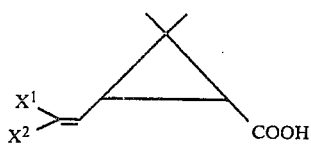

wherein $X^1$ and $X^2$ are the same or different and each is a halogen atom, a trichloromethyl group or a trifluoromethyl group, preferably $X^1$ is bromine or chlorine and $X^2$ is the same as $X^1$ or is a trifluoromethyl group, is prepared by heating the correponding bicyclic lactone (II) in the presence of a decarboxylation catalyst and a polar aprotic solvent.

Suitable catalysts include alkali metal salts, such as lithium iodide, bromide, chloride, selenide, thiocyanate, cyanide; sodium iodide, cyanide; potassium iodide, cyanide, and the like; amines such as triethylamine, 1,5-diazabicyclo-[3.4.0]non-;b 5-ene and the like; and silanes such as trimethylsilyl iodide and the like. Alkali metal iodides or cyanides are preferred.

Suitable solvents include polar aprotic solvents such as dimethyl sulfoxide, dimethylformamide, dimethylacetamide, hexamethylphosphortriamide, sulfolane, 1-methyl-2-pyrrolidone, and the like, and solvents such as pyridine, 2,6-lutidine, 2,4,6-collidone, and the like.

The reaction is suitably conducted at a temperature in the range of 60° C. to about 200° C.

The following examples illustrate preparation of 4,4-dimethyl-2H-pyran-2-one, the starting material for the present invention.

EXAMPLE 1

Preparation of ethyl 3,3-dimethyl-5-phenylthiopentanoate

A mixture of 60.0 g (0.384 mole) of ethyl 3,3-dimethyl-4-pentenoate and 90.0 g (0.817 mole) of benzenethiol was irradiated with a 100 watt incandescent light bulb at 120°-130° C. for 4 days. Benzoyl peroxide (1.8 g, 0.0074 mole) was added to the reaction vessel in 300 mg increments at various times throughout the 4-day irradiation period for a total of six such additions. distillation of the reaction mixture gave 102.3 g (96% yield) of ethyl 3,3-dimethyl-5-phenylthiopentanoate, 96.3% purity (glpc), bp 130° C./27 Pa (0.2 mm Hg).

EXAMPLE 2

Preparation of ethyl 5-chloro-3,3-dimethyl-5-phenylthiopentanoate

To a solution of 1.06 g (3.09 mmol) of ethyl 3,3-dimethyl-5-phenylthiopentanoate in 10 ml of carbon tetrachloride was added 590 mg (4.4 mmol) of 1-chloro-2,5-pyrrolidinedione, and the mixture was stirred at room temperature for 2 hours. The mixture was filtered, and the filtrate concentrated to give ethyl 5-chloro-3,3-dimethyl-5-phenylthio-pentanoate as an oil.

NMR Data (CDCl$_3$): δ(ppm): 1.10 (6H, s), 1.20 (3H, t), 2.10 (2H, d), 2.25 (2H, s), 4.02 (2H, q), 5.23 (1H, t), 7.00–7.53 (5H, m).

EXAMPLE 3

Preparation of ethyl 3,3-dimethyl-5-oxopentanoate from ethyl 5-chloro-3,3-dimethyl-5-phenylthiopentanoate The crude ethyl 5-chloro-3,3-dimethyl-5-phenylthiopentanoate from Example 2 was dissolved in 15 ml of acetone, and the solution was added to a mixture of 1.2 g (8.9 mmol) of cupric chloride and 1.2 g (15 mmol) of cupric oxide in 15 ml of acetone and 0.6 ml of water. The mixture was stirred at room temperature for 30 minutes, filtered, and the filtrate concentrated to give a residue. The residue was dissolved in methylene chloride, and the solution washed successively with an aqueous sodium bicarbonate solution and an aqueous solution of sodium chloride. The organic layer was separated, dried over anhydrous magnesium sulfate, filtered, and the filtrate concentrated to give 1.0 g of ethyl 3,3-dimethyl-5-oxopentanoate.

NMR Data (CCl$_4$): δ(ppm): 1.11 (6H, s), 1.23 (3H, t), 2.32 (2H, s), 2.45 (2H, b.s.), 4.05 (2H, q), 9.72 (1H, b.s.).

EXAMPLE 4

Preparation of 3,4-dihydro-4,4-dimethyl-2H-pyran-2-one

A solution of 11.16 g (0.065 mole) of ethyl 3,3-dimethyl-5-oxopentanoate and 11.2 g (0.073 mole) of phosphoryl chloride in 90 ml of toluene was heated under reflux for 14 hours. The mixture was diluted with ether, washed with an aqueous solution of sodium bicarbonate, dried over anhydrous magnesium sulfate, filtered, and the filtrate concentrated to give, after distillation, 3.29 g (40% yield) of 3,4-dihydro-4,4-dimethyl-2H-pyran-2-one, bp 105°–110° C./2670 Pa (20 mm Hg).

NMR Data (CDCl$_3$): δ(ppm): 1.10 (6H, s), 2.47 (2H, s), 5.12 (1H, d, J=6 Hz), 6.33 (1H, d, J=6 Hz).

The following examples illustrate conversion of 3,4-dihydro-4,4-dimethyl-2H-pyran-2-one to the intermediates of this invention by the claimed process.

EXAMPLE 5

Preparation of ethyl α,α,-3-trichloro-3,4,5,6-tetrahydro-4,4-dimethyl-6-oxo-2H-pyran-2-acetate A mixture of 3,4-dihydro-4,4-dimethyl-2H-pyran-2-one (2.6 g, 20.6 mmol), ethyl trichloroacetate (4.0 g, 20.9 mmol), and cuprous chloride (500 mg) was sealed in a test tube and heated at 150° for three days. At the end of this period the mixture was purified by column chromatography on silica gel to give 2.1 g of ethyl α,α,-3-trichloro-3,4,5,6-tetrahydro-4,4-dimethyl-6-oxo-2H-pyran-2-acetate (32% yield).

NMR data (CDCl$_3$): δ(ppm): 1.17 (6H,s), 1.35 (3H,t,J=7 Hz), 2.50 (1H,bd,J=17 Hz), 2.54 (1H,d,J=17 Hz), 4.16 (1H,d,J=7 hz), 4.32 (2H,q,J=7 Hz), 5.23 (1H,d,J=7 Hz).

EXAMPLE 6

Preparation of ethyl α,α-dichloro-6,6-dimethyl-4-oxo-3-oxabicyclo[3.1.0]hexane-2-acetate A solution of ethyl α,α,3-trichloro-3,4,5,6-tetrahydro-4,4-dimethyl-6-oxo-2H-pyran-2-acetate (3.43 g, 10.8 mmol) in 20 ml of tetrahydrofuran was cooled to −20° C. Potassium tert-butoxide was added in small portions while the mixture was stirred and maintained at −20° C. over a period of two hours. A total of 1.4 g (12.5 mmol) was added. Aqueous ammonium chloride was added and the mixture was extracted with methylene chloride. Purification by column chromatography gave 1.82 g of ethyl α,α-dichloro-6,6-dimethyl-4-oxo-3-oxabicyclo[3.1.0]hexane-2-acetate (60% yield).

NMR data (CDCl$_3$):
δ(ppm): 1.22 (6H,s), 1.34 (3H,t,J=7 Hz), 2.06 (1H,dd,J=1 Hz,6 Hz), 2.24 (1H,d,J=6 Hz, 4.31 (2H,Q,J=7 Hz), 4.80 (1H,bs).

EXAMPLE 7

Preparation of cis-3-(2,2-dichloroethenyl)-2,2-dimethylcyclopropanecarboxylic acid A mixture of ethyl, α,α-dichloro-6,6-dimethyl-4-oxo-3-oxabicyclo[3.1.0]hexane-2-acetate (500 mg, 1.78 mmol) and sodium iodide (500 mg, 3.3 mmol) in 4 ml of dimethyl sulfoxide was heated to 130° C. for 1.25 hours, cooled, and diluted with water. Sodium hydroxide (200 mg) was added and the mixture was washed with methylene chloride, acidified, and extracted with methylene chloride. The methylene chloride extract was concentrated to give 350 mg of an oil. Analysis by glpc with an internal standard showed that the oil contained 232 mg of cis-3-(2,2-dichloroethenyl)-2,2-dimethylcyclopropanecarboxylic acid (62% yield).

We claim:

1. A compound of the formula

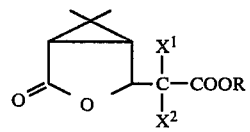

wherein $X^1$ and $X^2$ are the same or different and each is a halogen atom, a trichloromethyl group, or a trifluoromethyl group, and R is an alkyl group of 1 to 4 carbon atoms.

* * * * *